(12) United States Patent
Ouchi et al.

(10) Patent No.: US 8,167,800 B2
(45) Date of Patent: May 1, 2012

(54) APPARATUS AND METHOD FOR PROCESSING PULSE WAVES

(75) Inventors: Kazushige Ouchi, Saitama (JP); Takuji Suzuki, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 936 days.

(21) Appl. No.: 12/167,586

(22) Filed: Jul. 3, 2008

(65) Prior Publication Data

US 2009/0018408 A1 Jan. 15, 2009

(30) Foreign Application Priority Data

Jul. 5, 2007 (JP) ................................. 2007-177173

(51) Int. Cl.
*A61B 5/0245* (2006.01)
*G06F 19/00* (2011.01)
(52) U.S. Cl. ......................................... 600/301; 702/19
(58) Field of Classification Search ........................ None
See application file for complete search history.

(56) References Cited

U.S. PATENT DOCUMENTS 7,351,206 B2 4/2008 Suzuki et al.
7,608,046 B2 * 10/2009 Suzuki et al. ................. 600/500
2005/0038327 A1 * 2/2005 Tanaka et al. ................. 600/301
2005/0234314 A1 * 10/2005 Suzuki et al. ................. 600/301
2008/0027331 A1 1/2008 Suzuki et al.

FOREIGN PATENT DOCUMENTS

| JP | 06302511 | 8/1998 |
|---|---|---|
| JP | 2001-61795 | 3/2001 |
| JP | 2002-17694 | 1/2002 |
| JP | 2005-95653 | 4/2005 |
| JP | 2005-160640 | 6/2005 |

OTHER PUBLICATIONS

U.S. Appl. No. 12/208,769, filed Sep. 11, 2008, Yokoyama, et al.
U.S. Appl. No. 12/212,182, filed Sep. 17, 2008, Suzuki.
U.S. Appl. No. 12/341,225, filed Dec. 22, 2008, Ouchi, et al.

* cited by examiner

*Primary Examiner* — John S Brusca
(74) *Attorney, Agent, or Firm* — Oblon, Spivak, McClelland, Maier & Neustadt, L.L.P.

(57) ABSTRACT

Pulse wave signal data expressing the pulse wave of a subject and body movement signal data expressing body movements of the subject are obtained so that a correlation coefficient expressing the degree of correlation between the pulse wave signal data and the body movement signal data is calculated. One or more pieces of the pulse wave signal data in which the correlation coefficient is equal to or larger than a predetermined threshold value are eliminated.

14 Claims, 13 Drawing Sheets

APPARATUS AND METHOD FOR PROCESSING PULSE WAVES

CROSS-REFERENCE TO RELATED APPLICATIONS

This application is based upon and claims the benefit of priority from the prior Japanese Patent Application No. 2007-177173, filed on Jul. 5, 2007; the entire contents of which are incorporated herein by reference.

BACKGROUND OF THE INVENTION

1. Field of the Invention

The present invention relates to a pulse wave processing apparatus and a pulse wave processing method for processing pulse wave signals as data.

2. Description of the Related Art

An example of biomarkers that prominently reflect the state of a subject is heartbeats (e.g., autonomic nerve activities based on analysis of heartbeat rates and frequencies of heartbeat intervals). Electrocardiography is commonly used to measure heartbeats directly. To perform electrocardiography, it is necessary to paste electrodes on the subject in, for example, a number of places on the chest. The subject is greatly burdened if he/she needs to have the electrodes attached to his/her body all the time while he/she leads his/her daily life. Accordingly, the pulse waves on fingers, wrists, and earlobes are used as biomarkers that can be obtained more easily and are equivalent to heartbeats. However, a problem arises where, when pulse waves are measured, the waveforms are more greatly influenced and disturbed by movements of the body (hereinafter "body movements") than when electrocardiography is used. To cope with this problem, techniques for eliminating body movement influences from the waveforms of the pulse waves have been proposed (see, for example, Japanese Patent No. 2816944, JP-A 2001-61795 (KOKAI), JP-A 2002-17694 (KOKAI), JP-A 2005-95653 (KOKAI), and JP-A 2005-160640 (KOKAI)).

According to the techniques disclosed in these documents, in principle, body movement components are eliminated from the characteristics of the pulse wave signal or from the characteristics of the pulse wave signal and the body movement signal within a predetermined section, so that the average pulse rate for the section can be calculated. These techniques are suitable for the use during physical exercises; however, in the case where the body movement signal and the pulse wave signal are in substantially the same frequency bandwidth, a problem remains where it is difficult to eliminate the body movement components. Also, it is not possible to use these techniques for the purpose of extracting the interval for each pulse beat of the pulse wave and performing an autonomic nerve analysis based on an analysis of the frequency of the fluctuation component.

On the other hand, there is another method for judging, depending on how large body movements are, whether each of parts of the pulse wave that are obtained when the body movements were made should be used in the analysis or not. According to this method, it is possible to judge whether each of the parts of the pulse wave should be used or not in correspondence with each pulse beat; however, in the case where a body movement that exceeds a predetermined magnitude is made, there is a possibility that all of the parts of the pulse wave may be judged to be unusable, and even some parts of the data that properly express the measured pulse wave may be lost. To perform an autonomic nerve analysis with a high level of precision, it is desirable to use as large a part of the data that correctly expresses the measured pulse wave as possible.

SUMMARY OF THE INVENTION

According to one aspect of the present invention, a pulse wave processing apparatus includes an obtaining unit that obtains pulse wave signal data expressing a pulse wave of a subject and body movement signal data expressing body movements of the subject; a correlation coefficient calculating unit that calculates a correlation coefficient expressing a degree of correlation between the pulse wave signal data and the body movement signal data; and a pulse wave eliminating unit that eliminates one or more pieces of the pulse wave signal data in which the correlation coefficient is equal to or larger than a predetermined threshold value.

According to another aspect of the present invention, a pulse wave processing method executed by a pulse wave processing apparatus that includes an obtaining unit, a correlation coefficient calculating unit, and a pulse wave eliminating unit, the method includes obtaining pulse wave signal data expressing a pulse wave of a subject and body movement signal data expressing body movement of the subject by employing the obtaining unit; calculating a correlation coefficient expressing a degree of correlation between the pulse wave signal data and the body movement signal data by employing the correlation coefficient calculating unit; and eliminating one or more pieces of the pulse wave signal data in which the correlation coefficient is equal to or larger than a predetermined threshold value by employing the pulse wave eliminating unit.

DETAILED DESCRIPTION OF THE INVENTION

Figure 1:
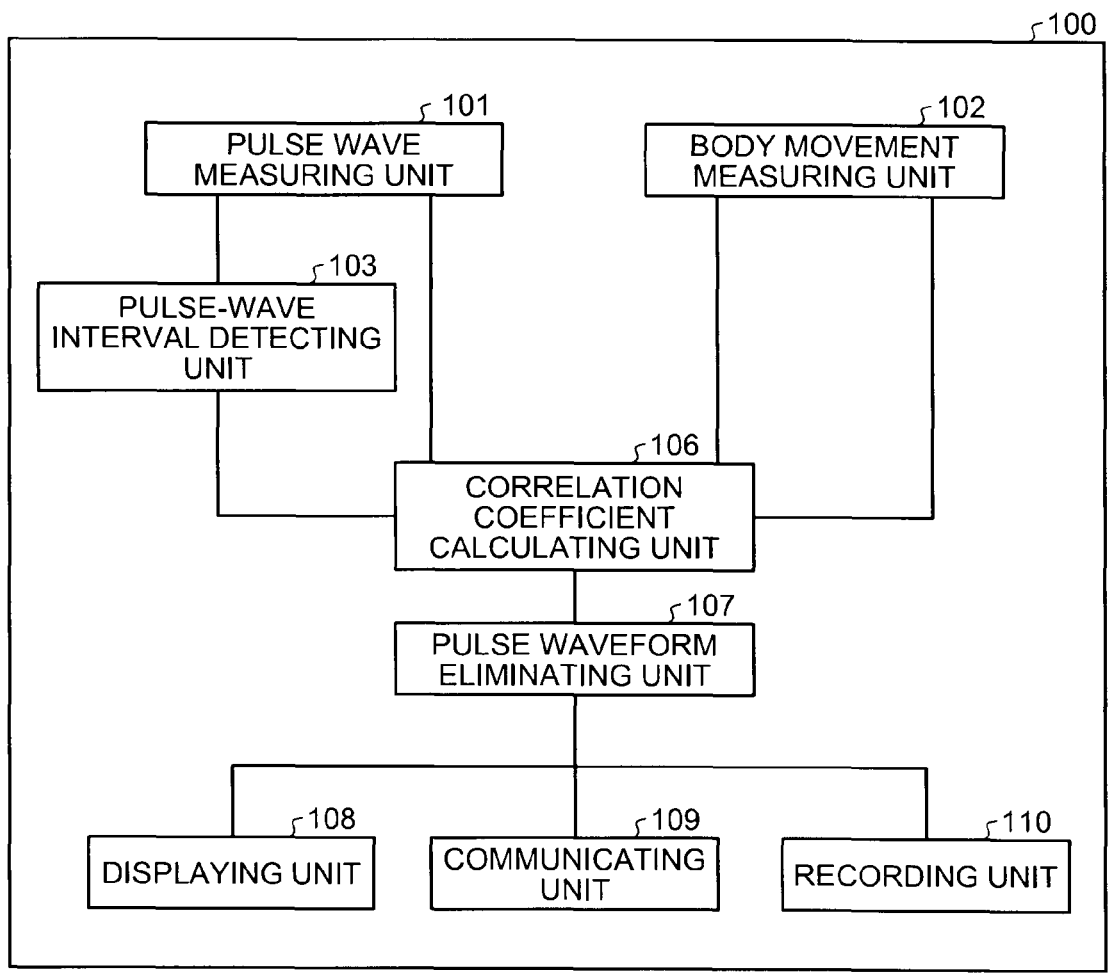
FIG. 1 is a block diagram of a pulse wave processing apparatus according to an embodiment of the present invention.

FIG. 1 is a block diagram of a pulse wave processing apparatus 100 according to an exemplary embodiment of the present invention. As shown in FIG. 1, the pulse wave processing apparatus 100 includes a pulse wave measuring unit 101, a body movement measuring unit 102, a pulse-wave interval detecting unit 103, a correlation coefficient calculating unit 106, a pulse waveform eliminating unit 107, a displaying unit 108, a communicating unit 109, and a recording unit 110.

Figure 2:
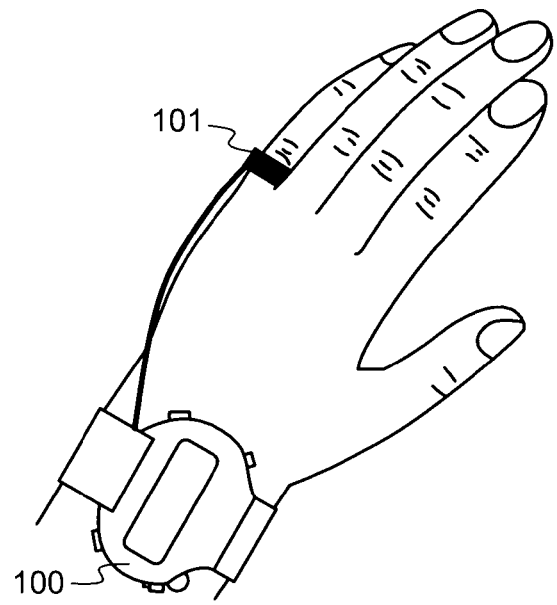
FIG. 2 is a drawing illustrating an example of the exterior appearance of the pulse wave processing apparatus and how it is attached to a subject.

FIG. 2 is a drawing illustrating an example of the exterior appearance of the pulse wave processing apparatus 100 and how it is attached to a subject. In this example, the pulse wave processing apparatus 100 is worn around a wrist like a wrist watch. The pulse wave measuring unit 101 is wound around a finger so that the pulse wave is measured at the finger abdomen.

Figure 3:
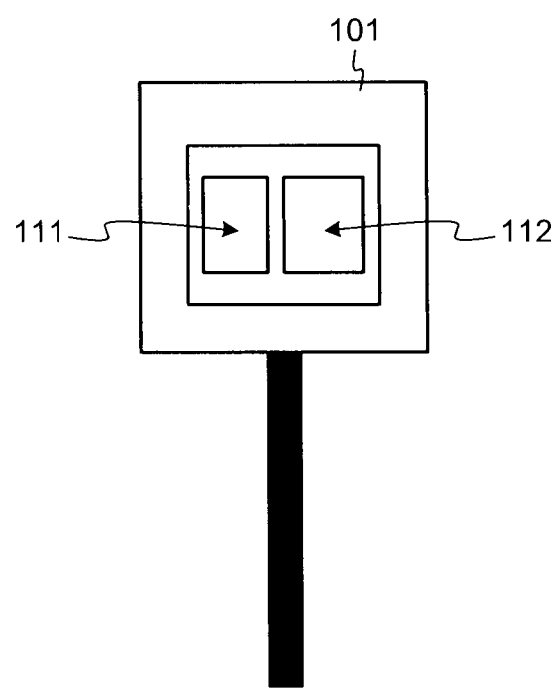
FIG. 3 is a schematic drawing illustrating a pulse wave measuring unit.
Figure 4:
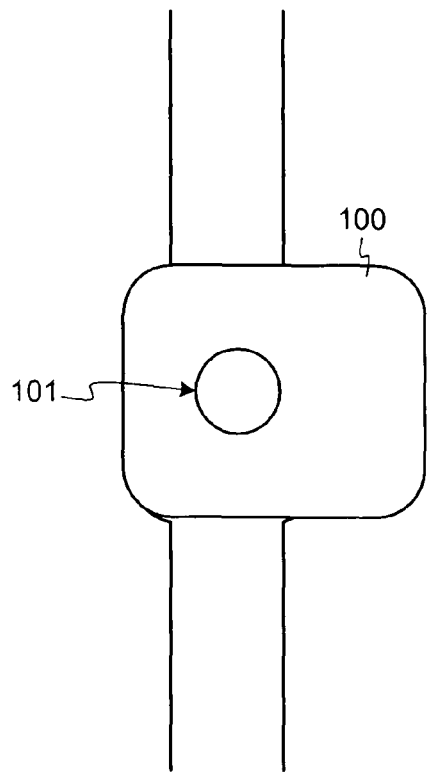
FIG. 4 is a drawing illustrating an example in which the pulse wave processing apparatus has the pulse wave measuring unit provided on the lower face thereof.
Figure 5:
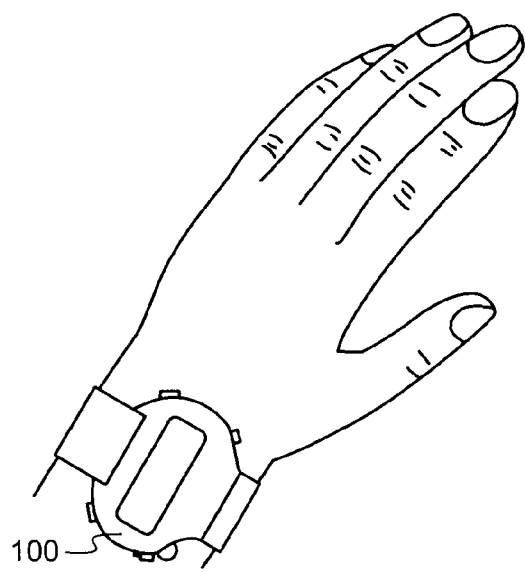
FIG. 5 is a drawing illustrating an example in which the pulse wave processing apparatus shown in FIG. 4 is worn around a wrist like a wrist watch.
Figure 6:
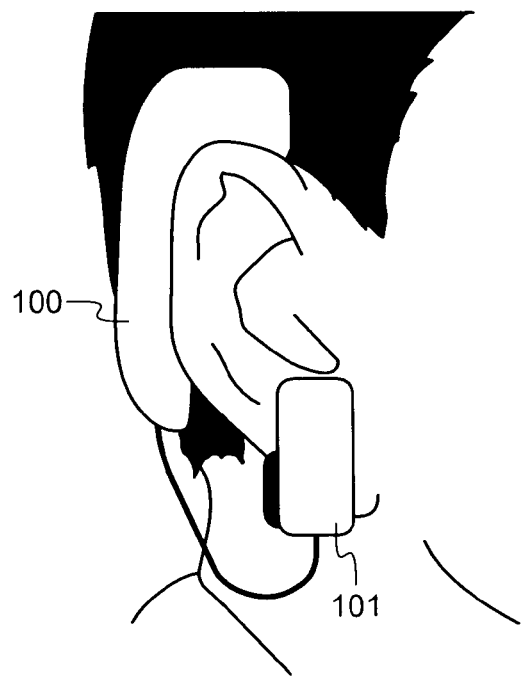
FIG. 6 is a drawing illustrating an example in which the pulse wave processing apparatus is configured so as to be wearable on an ear.

FIG. 3 is a schematic drawing illustrating the pulse wave measuring unit 101. The pulse wave measuring unit 101 includes a photoelectric pulse wave sensor that is made up of a combination of a Light Emitting Diode (LED) 111 and a photodiode 112. In the pulse wave measuring unit 101, the LED 111 radiates light onto the skin of the subject, and the photodiode 112 detects changes in the intensity of the reflected light (or the transmitted light) that is caused by changes in the bloodstream and obtains the detected changes in the intensity as a pulse wave. The pulse wave measuring unit 101 thus measures the pulse wave and outputs a pulse wave signal expressing the measured pulse wave. The color of the LED 111 may be selected from blue, green, red, and near-infrared for which blood hemoglobin has a good light absorption characteristic. As the photodiode 112, it is preferable to select one having a characteristic that is suitable for the wavelength range of the LED 111 being used. FIG. 4 is a drawing illustrating an example in which the pulse wave processing apparatus 100 has the pulse wave measuring unit 101 provided on the lower face thereof. FIG. 5 is a drawing illustrating an example in which the pulse wave processing apparatus 100 shown in FIG. 4 is worn around a wrist like a wrist watch. In this example, the pulse wave is measured in the wrist portion of the subject. In this situation, the pulse wave measuring unit 101 may be configured with the photoelectric pulse wave sensor that is made up of the combination of the LED 111 and the photodiode 112 as shown in FIG. 3. Alternatively, the pulse wave measuring unit 101 may be configured with a pressure sensor that detects changes in the arterial pulsation based on the pressure. FIG. 6 is a drawing illustrating an example in which the pulse wave processing apparatus 100 is configured so as to be wearable on an ear. In this example, the pulse wave is measured while the pulse wave measuring unit 101 is worn on the subject's earlobe. In this situation, it is desirable to configure the pulse wave measuring unit 101 with a photoelectric pulse wave sensor that is made up of the combination of the LED 111 and the photodiode 112 as shown in FIG. 3.

Returning to FIG. 1, the pulse-wave interval detecting unit 103 detects intervals between the pulse beats by sampling the pulse wave signal that has been output from the pulse wave measuring unit 101. More specifically, the pulse-wave interval detecting unit 103 includes filters like a finite impulse response (FIR) filter, a Low-Pass Filter (LPF), and a High-Pass Filter (HPF). The pulse-wave interval detecting unit 103 detects the intervals between the pulse beats after eliminating noise components (e.g., undesired noises and fluctuations in the base line) other than the pulse wave and performing signal processing so as to, for example, steepen the pulse waveform.

The body movement measuring unit 102 includes, for example, a three-axis acceleration sensor that detects accelerations in the three axial directions along the x-axis, the y-axis, and the z-axis. While the three-axis acceleration sensor is attached to a predetermined part of the human body, the body movement measuring unit 102 measures the accelerations in the three axial directions as body movements of the subject and outputs the measured accelerations as a body movement signal. Each of the accelerations in the three axial directions corresponds to a different one of component signals. To detect the accelerations by using an acceleration sensor, it is acceptable to use any type of acceleration sensor such as a piezoresistance type, a piezoelectric type, a capacitance type, or else.

The detailed configurations of the pulse wave measuring unit 101, the pulse-wave interval detecting unit 103, and the body movement measuring unit 102 are described in, for example, JP-A 2001-344352 (KOKAI).

Based on the pulse wave intervals that have been detected by the pulse-wave interval detecting unit 103, the correlation coefficient calculating unit 106 determines an applicable range of the pulse wave that is to be used for calculating correlation coefficients. The correlation coefficient calculating unit 106 then calculates, within a temporal sequence, the correlation coefficients by using the part of the pulse wave signal expressing the pulse wave within the applicable range and the part of the body movement signal expressing the body movements that have been measured by the body movement measuring unit 102 in the same period of time as the part of the pulse wave within the applicable range was measured.

The pulse-wave interval detecting unit 103 and the correlation coefficient calculating unit 106 obtain the pulse wave signal that has been output from the pulse wave measuring unit 101 and the body movement signal that has been output from the body movement measuring unit 102, via an input port (not shown) that is hardware serving as an obtaining unit.

The pulse waveform eliminating unit 107 eliminates one or more parts of the data expressing the pulse wave intervals (hereinafter, the "pulse wave interval data") corresponding to any period of time in which the correlation coefficients that have been calculated by the correlation coefficient calculating unit 106 are each equal to or larger than a first threshold value. On the contrary, the pulse waveform eliminating unit 107 adopts one or more parts of the pulse wave interval data corresponding to any period of time in which the correlation coefficients are each smaller than the first threshold value.

Figure 7:
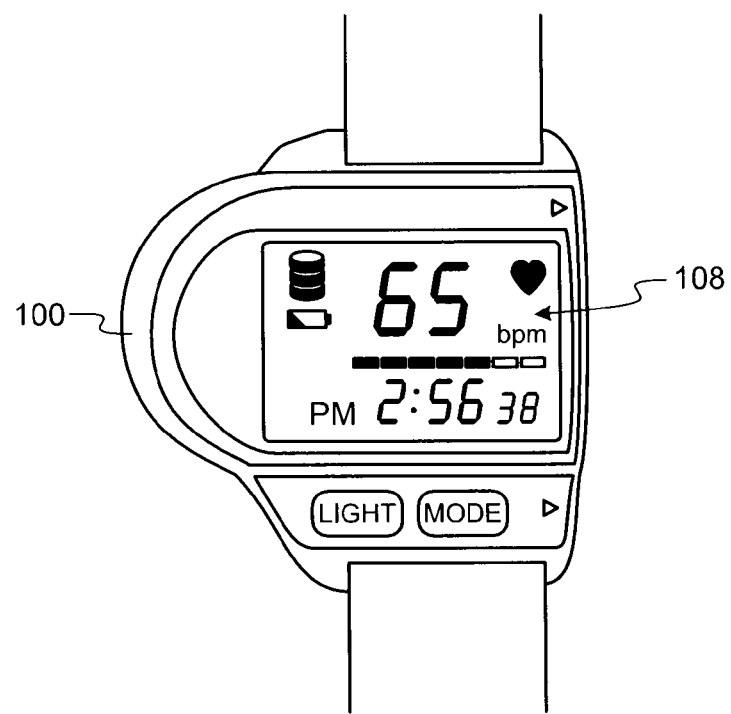
FIG. 7 is a drawing illustrating an example in which a displaying unit is provided on the upper face of the pulse wave processing apparatus.

The displaying unit 108 is configured with a liquid crystal display (LCD) or the like that is operable to display the one or more parts of the data expressing the pulse wave intervals (i.e., the pulse wave interval data) detected by the pulse-wave interval detecting unit 103 that have been adopted by the pulse waveform eliminating unit 107. FIG. 7 is a drawing illustrating an example in which the displaying unit 108 is provided on the upper face of the pulse wave processing apparatus 100.

The recording unit 110 is a storage area that stores therein various types of measured data that have been measured in the pulse wave processing apparatus 100. For example, the recording unit 110 may be configured with a flash memory or an Electrically Erasable and Programmable Read-Only Memory (EEPROM). Examples of the measured data include the pulse wave signal, the body movement signal, and the pulse wave interval data.

The communicating unit 109 transfers the measured data to an external terminal through a wireless communication (that uses, for example, electromagnetic waves or light) like a Bluetooth communication or an infrared communication or through a wired communication that uses, for example, a Universal Serial Bus (USB) or the Recommended Standard 232 Version C (RS-232C). The communicating unit 109 may transfer the measured data every time a measuring process has been performed. Alternatively, another arrangement is acceptable in which the measured data is stored into the recording unit 110 and collectively transferred.

Figure 8:
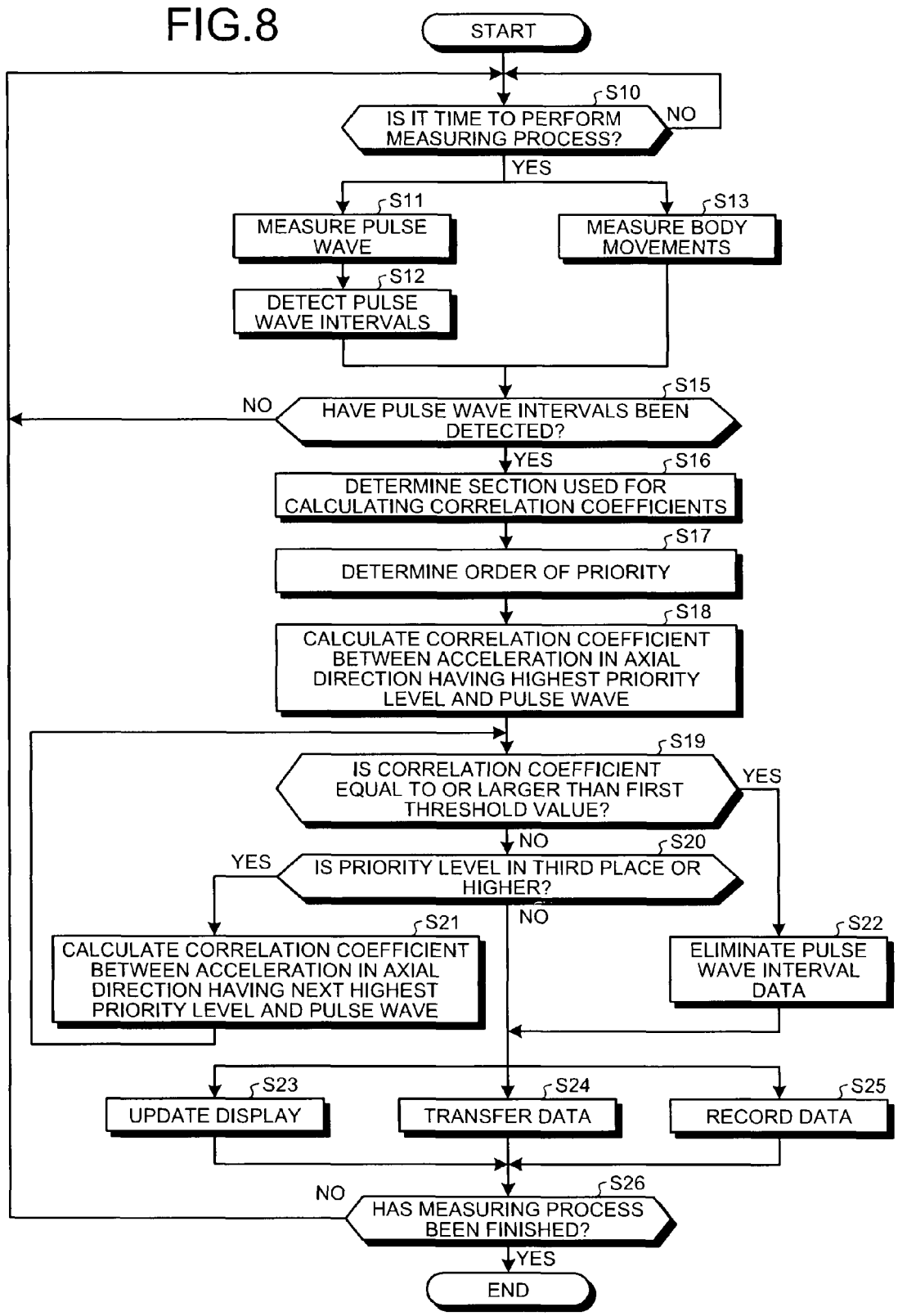
FIG. 8 is a flowchart of a procedure in a pulse wave measuring process performed by the pulse wave processing apparatus.

Next, an operation performed by the pulse wave processing apparatus 100 according to an embodiment of the present invention will be explained. FIG. 8 is a flowchart of a procedure in the pulse wave measuring process performed by the pulse wave processing apparatus 100. An example in which the pulse wave processing apparatus 100 is worn around a wrist as shown in FIG. 2 or FIG. 5 will be explained. First, when the subject instructs that the process to measure the pulse wave should be started by operating an electric power switch (not shown) or a measuring process start button (not shown) of the pulse wave processing apparatus 100 (step S10), the pulse wave measuring unit 101 measures the pulse wave in a predetermined sampling cycle (step S11). The sampling cycle may be, for example, 50 milliseconds (ms). After that, the pulse-wave interval detecting unit 103 performs a pulse wave interval detecting process by using a pulse wave signal that has been obtained by the pulse wave measuring unit 101 by performing the measuring process (step S12).

Figure 9:
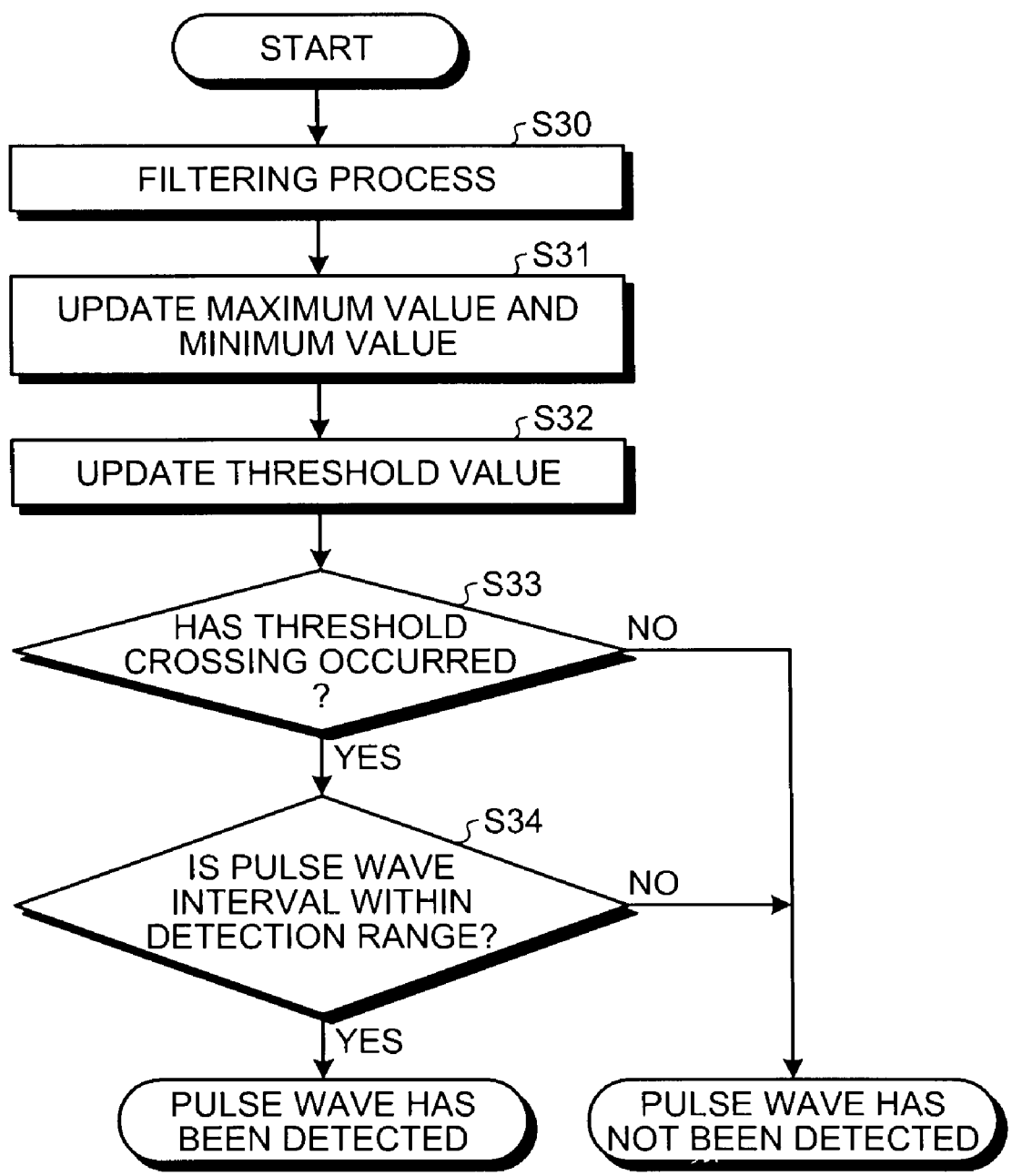
FIG. 9 is a flowchart of a procedure in a pulse wave interval detecting process.

FIG. 9 is a flowchart of a procedure in the pulse wave interval detecting process performed by the pulse-wave interval detecting unit 103. First, according to a filter characteristic depending on the hardware configuration of the pulse wave measuring unit 101, the pulse-wave interval detecting unit 103 performs, as necessary, a digital filtering process by using, for example, the finite impulse response (FIR) filter. Further, as needed, by using one or both of the Low-Pass Filter (LPF) and the High-Pass Filter (HPF), the pulse-wave interval detecting unit 103 performs a process to eliminate noise components (e.g., undesired noises and fluctuations in the base line) other than the pulse wave and a process to steepen the pulse waveform (step S30). Subsequently, the pulse-wave interval detecting unit 103 updates the maximum value and the minimum value of the pulse waveform during a predetermined period of time (e.g., 1.5 seconds) before the current sampling period (step S31). The pulse-wave interval detecting unit 103 determines a second threshold value (e.g., a midpoint between the maximum value and the minimum value) that is used for detecting crossing points (i.e., threshold crossing points) of the pulse waveform (step S32). It is desirable to specify the second threshold value according to the measuring system being used because the characteristics (e.g., the shape, the polarity, etc.) of the waveform may vary depending on the measuring system. Performing the process to determine the second threshold value makes it easy to dynamically follow the changes in the amplitude of the pulse wave.

Figure 10:
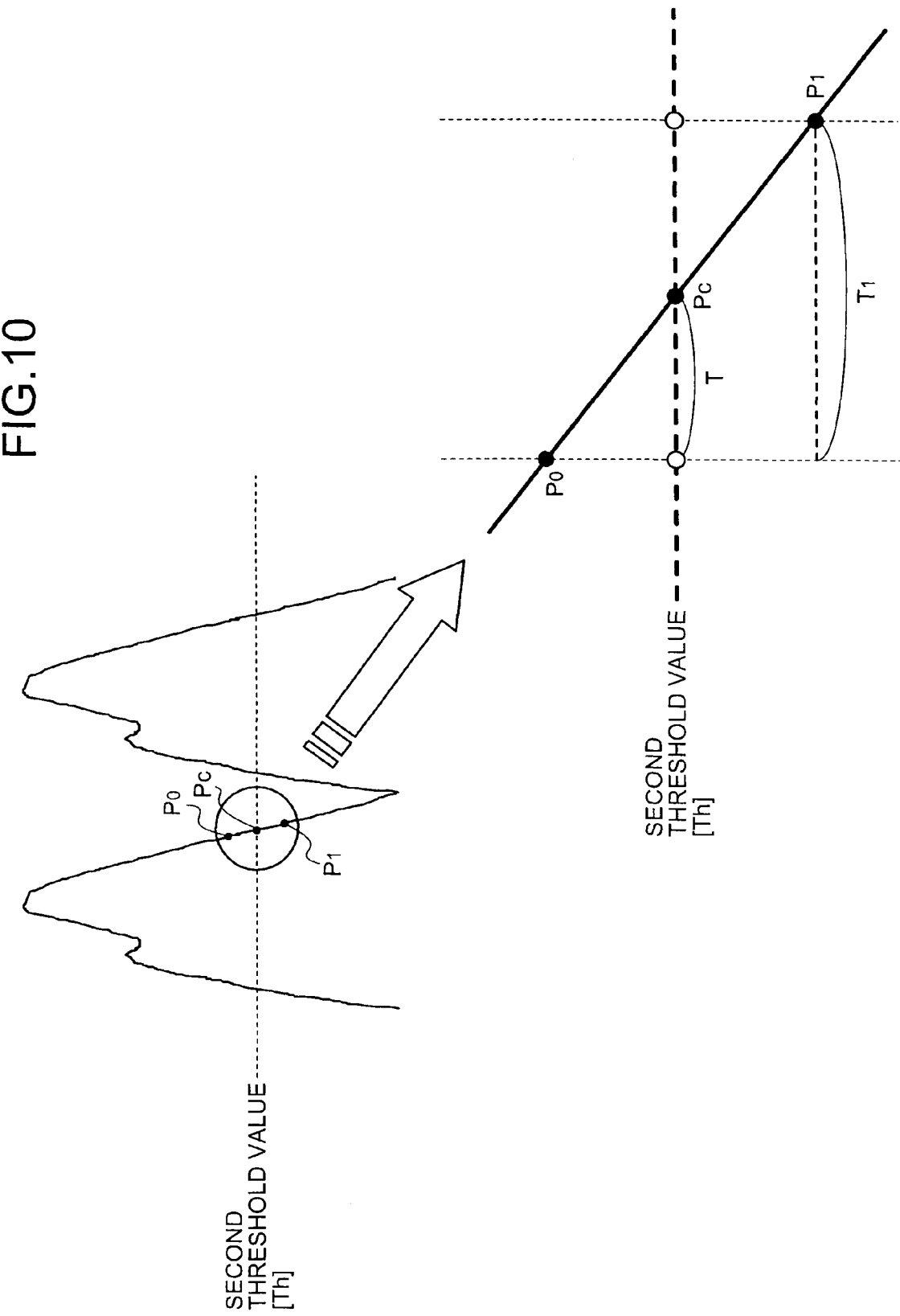
FIG. 10 is a drawing illustrating an example of an approximation process performed on a threshold crossing point.

Next, the pulse-wave interval detecting unit 103 judges whether the pulse waveform has crossed the specified second threshold value (in a predetermined direction). The pulse-wave interval detecting unit 103 determines that the first sampling point in time at which the pulse waveform crosses the second threshold value as a time at which a pulse wave interval should be detected (step S33). In this situation, because the threshold crossing point is between two sampling points in time, there is a difference between the times at which the sampling is performed and the actual threshold crossing point in time. To cope with this situation, it is a good idea to perform an approximation process on the threshold crossing point so as to make the influence of the difference smaller. FIG. 10 is a drawing illustrating an example of the approximation process performed on a threshold crossing point. In the approximation process shown in FIG. 10, it is presumed that the pulse waveform between the two sampling points in time (i.e., between P0 and P1) is a straight line, so that a threshold crossing point Pc can be estimated by using the ratio of the amplitude before and after the second threshold value (Th). In the example shown in FIG. 10, the following expression is satisfied:

$$T=T1 \times (P0-Th)/(P0-P1)$$

The threshold crossing point Pc is calculated by using T in the expression. Accordingly, it is possible to detect the pulse wave interval. There is, however, a possibility that the pulse wave may contain noises or the pulse wave signal has not correctly been measured. To cope with this problem, the pulse-wave interval detecting unit 103 judges whether the detected pulse wave interval is within a pulse rate range (e.g., the pulse rate is between 40 beats per minute [bpm] to 120 [bpm], which means that the pulse wave interval is in the range of 0.5s to 1.5s) that is presumed in advance (step S34). In the case where the detected pulse wave interval is not within the presumed range (step S34: No), the pulse-wave interval detecting unit 103 assumes that the pulse wave interval has not properly been detected. On the contrary, in the case where the detected pulse wave interval is within the presumed range (step S34: Yes), the pulse-wave interval detecting unit 103 assumes that the pulse wave interval has been detected.

On the other hand, at step S13 in FIG. 8, the body movement measuring unit 102 measures body movements of the subject. In the present example, because the body movement measuring unit 102 includes the three-axis acceleration sensor, the body movement measuring unit 102 measures the accelerations in the three axial directions and outputs the measured accelerations as the body movement signal. According to the present embodiment, the magnitude of the influence of postures and/or movements of the subject on the pulse waveform is measured based on the accelerations in the mutually different axial directions. After that, that process proceeds to step S15.

At step S15, the correlation coefficient calculating unit 106 judges whether the pulse-wave interval detecting unit 103 has detected a pulse wave interval as a result of performing the pulse wave interval detecting process described above. In the case where the result of the judging process is in the affirmative, the process proceeds to step S16. On the contrary, in the case where the result of the judging process is in the negative, the process returns to step S10.

Figure 11:
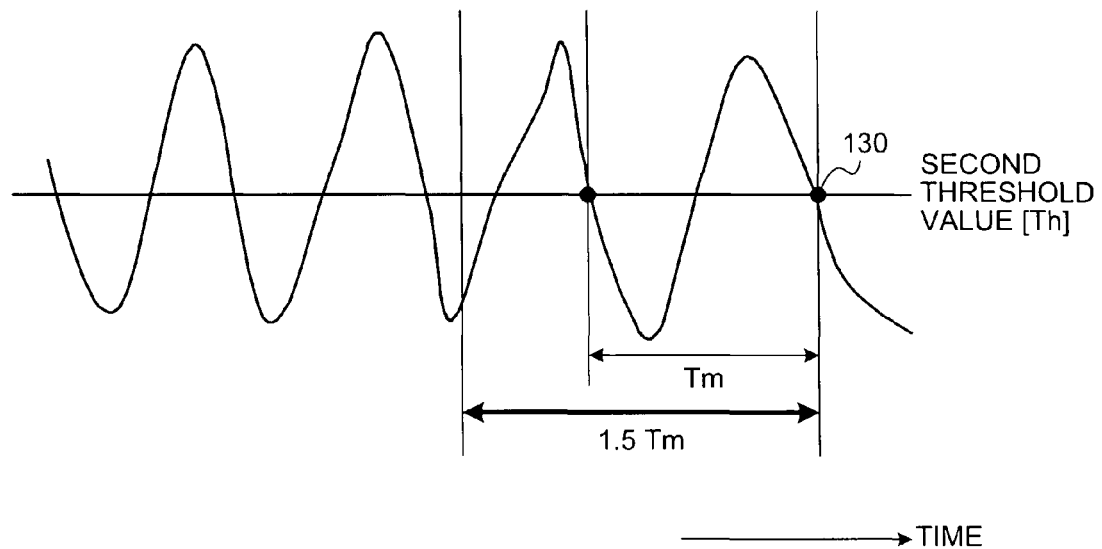
FIG. 11 is a drawing illustrating an example of an applicable range of a pulse wave signal that is to be used for calculating correlation coefficients.

At step S16, the correlation coefficient calculating unit 106 determines an applicable range of the pulse wave signal that is to be used for calculating the correlation coefficients. The applicable range should be determined so that it sufficiently includes the one pulse wave interval at the current point in time that has been detected by the pulse-wave interval detecting unit 103 as a result of performing the pulse wave interval detecting process at step S12 described above. For example, the applicable range should be determined so as to be 1.5 times longer than the pulse wave interval. FIG. 11 is a drawing illustrating an example of an applicable range of the pulse wave signal that is to be used for calculating the correlation coefficients. In the case where the pulse-wave interval detecting unit 103 detects the pulse wave interval while using the second threshold value (Th) as a reference, every time a pulse beat is detected, a section that extends into the past from the most recent detection trigger point (i.e., the threshold crossing point) 130 and that has a length (1.5 Tm) that is 1.5 times longer than the most recent pulse wave interval (Tm) is specified as the applicable range to be used for calculating the correlation coefficients. Every time one pulse wave interval is detected, the correlation coefficient calculating unit 106 makes an adjustment to the applicable range by following the procedure described above so as to specify a new applicable range.

After that, at step S17, the correlation coefficient calculating unit 106 determines an order of priority for the accelerations in the three axial directions that have been output from the body movement measuring unit 102 as the body movement signal, the order of priority being used for calculating the correlation coefficients. This process is performed because the axial direction of the acceleration that influences the pulse waveform may vary depending on postures and/or movements of the subject. For example, between the accelerations that are measured while the subject is walking with a normal swing of the arms and the accelerations that are measured while the subject is walking while carrying an object in his/her arms, the axial direction that influences the pulse waveform is different. The influence related to an impact caused by the subject's soles touching the ground during the walk is large, and also the degree of correlation between the direction of the gravity acceleration (i.e., the direction perpendicular to the ground) that has been detected by the three-axis acceleration sensor and the acceleration fluctuation waveform is high. Thus, the correlation coefficient calculating unit 106 compares the direct current components of the accelerations in the three axial directions with one another, the accelerations having been measured by the body movement measuring unit 102 that includes the three-axis acceleration sensor. The correlation coefficient calculating unit 106 then determines the order of priority, based on how close each of the components is to ±1G, which is the gravity acceleration. For example, in the example shown in FIG. 14, the acceleration in the Y-axis direction has the highest priority level (i.e., it is in first place), whereas the acceleration in the Z-axis direction has the second highest priority level (i.e., it is in second place), and the acceleration in the X-axis direction has the third highest priority level (i.e., it is in third place). After that, the correlation coefficient calculating unit 106 first calculates a correlation coefficient between the part of the pulse wave signal within the applicable range that has been determined at step S16 and the acceleration in one of the axial directions that has the highest priority level (e.g., the Y-axis direction in the present example) among the accelerations that have been measured by the body movement measuring unit 102 substantially in the same period of time as the part of the pulse wave within the applicable range was measured (step S18). To calculate the correlation coefficient, for example, the Fast Fourier Transform (FFT) method or a convolution method may be used.

Subsequently, the correlation coefficient calculating unit 106 judges whether the calculated correlation coefficient is equal to or larger than a first threshold value that is determined in advance (step S19). In the case where the result of the judging process at step S19 is in the affirmative, the pulse waveform eliminating unit 107 eliminates the pulse wave interval data that has been detected at step S12 (step S22), and the process proceeds to steps S23, S24, and S25. On the contrary, in the case where the result of the judging process at step S19 is in the negative, the correlation coefficient calculating unit 106 judges whether the acceleration in the axial direction having the next highest priority level is in third place or higher (step S20). In the case where the result of the judging process at step S20 is in the affirmative, the correlation coefficient calculating unit 106 calculates a correlation coefficient between the part of the pulse wave signal within the applicable range that has been determined at step S16 and the acceleration in another one of the axial directions that has the next highest priority level among the accelerations that have been measured by the body movement measuring unit 102 substantially in the same period of time as the part of the pulse wave within the applicable range was measured (step S21). On the contrary, in the case where the result of the judging process at step S20 is in the negative, the pulse wave interval data that has been detected at step S12 will not be eliminated, and the process proceeds to steps S23, S24, and S25.

Figure 12:
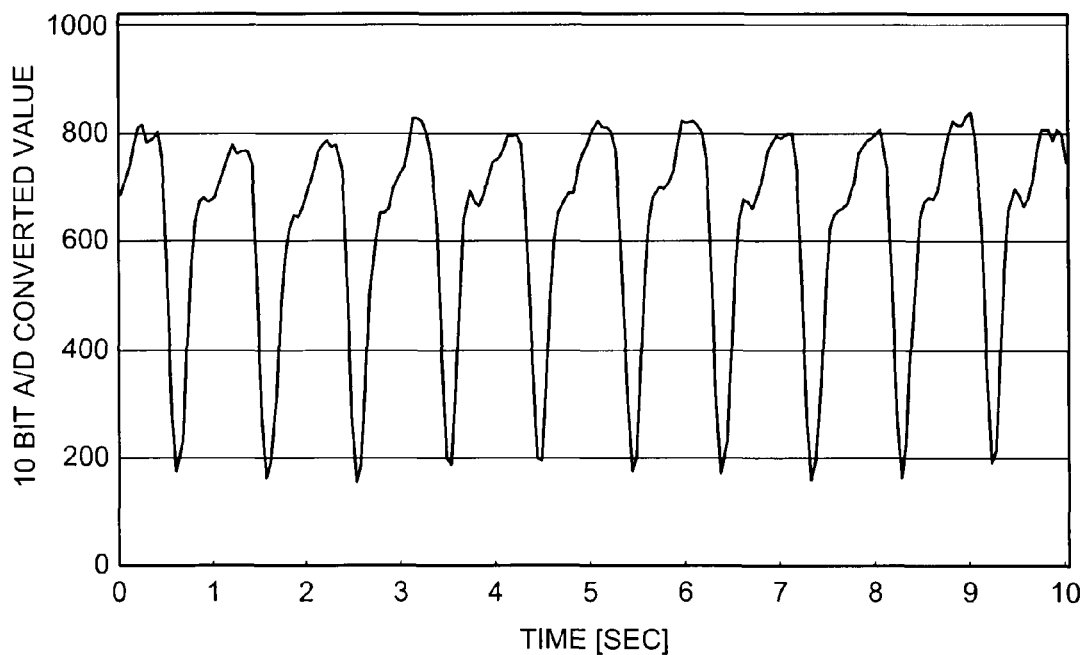
FIG. 12 is a drawing illustrating an example of a pulse waveform that is obtained while the subject is at rest.
Figure 13:
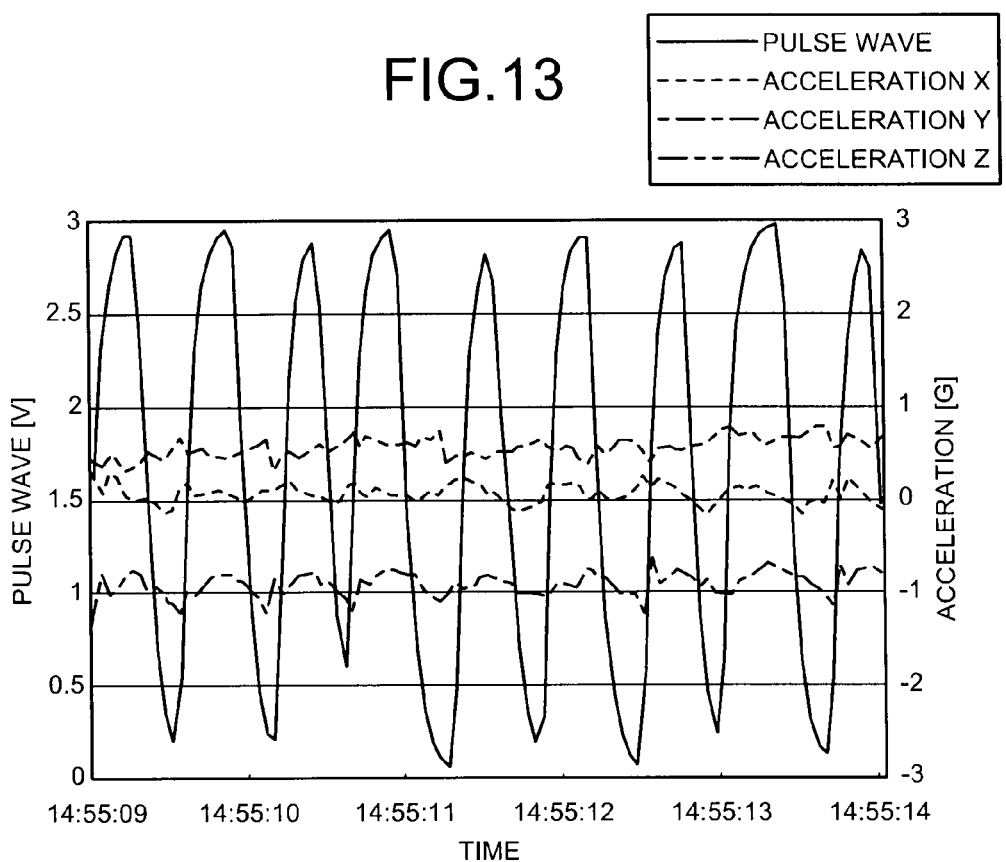
FIG. 13 is a drawing illustrating an example of a pulse waveform and acceleration waveforms in three axial directions that are obtained while the subject is walking and carrying document files in his/her arms.
Figure 14:
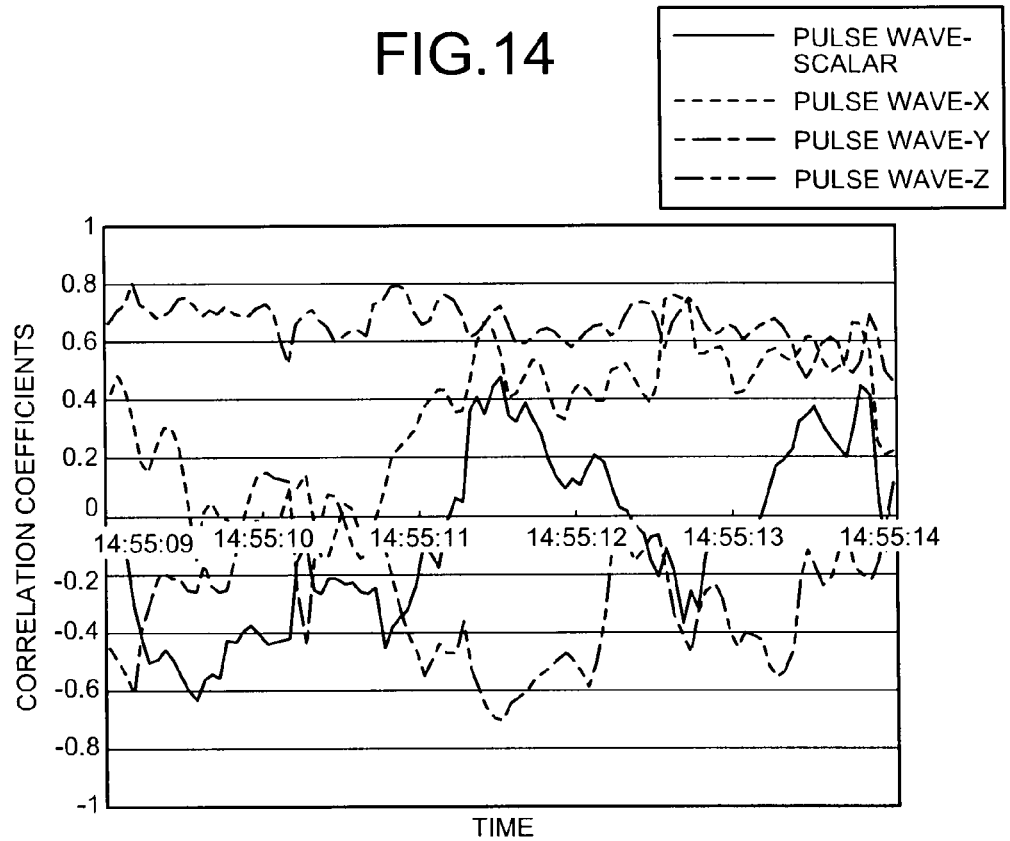
FIG. 14 is a drawing illustrating correlation coefficients between the pulse waveform and the acceleration waveforms in the three axial directions.

Next, the process will be explained further in detail, with reference to the examples of waveforms in the drawings. FIG. 12 is a drawing illustrating an example of a pulse waveform that is obtained while the subject is at rest. FIG. 13 is a drawing illustrating an example of a pulse waveform and acceleration waveforms in the three axial directions that are obtained while the subject is walking and carrying document files in his/her arms. The direction that is perpendicular to the ground is the Y-axis. FIG. 14 is a drawing illustrating correlation coefficients between the pulse waveform and the acceleration waveforms in the three axial directions. As the pulse waveform shown in FIG. 12 is compared with the pulse waveform shown in FIG. 13, it is observed that the waveforms are similar to each other. Thus, when conventional techniques are used, there is a possibility that the pulse waveform shown in FIG. 13 may be detected as a waveform that expresses the actual pulse wave of the subject. However, by referring to the correlation coefficients shown in FIG. 14, it is understood that the degree of correlation between the pulse waveform and the acceleration waveform in the Y-axis direction (i.e., the direction perpendicular to the ground) is maintained at a high level. Accordingly, it is understood that the pulse waveform shown in FIG. 13 is not a waveform that expresses the actual pulse wave of the subject but is a waveform that is influenced by body movements (i.e., walking, in the present example) of the subject. With the example shown in FIG. 14, if the first threshold value is specified in advance so as to be around "0.6", the pulse waveform eliminating unit 107 is able to eliminate any parts of the pulse wave interval data that correspond to one or more parts of the pulse waveform that are greatly influenced by the body movements of the subject, as a result of the judging process at step S11 described above.

As explained above, the parts of the waveform that express the actual pulse wave and the parts of the waveform that are greatly influenced by the body movements are distinguished from each other, so that the parts of the data that correspond to the former are adopted as the pulse wave interval data. The adopted parts of the pulse wave interval data may be displayed by the displaying unit 108 every time the data is obtained (step S23), or may be transmitted to an external information terminal by the communicating unit 109 every time the data is obtained (step S24), or may be temporarily stored in the recording unit 110 (step S25). Another arrangement is also acceptable in which the pulse wave interval data that has been stored and accumulated in the recording unit 110 is collectively transferred to an external information terminal by the communicating unit 109. When the measuring process has been finished (step S26: Yes), the process ends.

With the configurations as described above, by using the correlations between the pulse wave signal and the body movement signal, it is possible to judge whether any part of the pulse wave signal is influenced by the body movements. Thus, it is possible to eliminate any part of the pulse wave signal that is greatly influenced by the body movements and from which it is not possible to correctly detect the pulse wave intervals. At the same time, it is possible to adopt as large a part of the pulse wave signal from which pulse wave intervals can correctly be detected as possible. As a result, by eliminating any parts of the pulse wave interval data that are greatly influenced by the body movements and adopting the parts of the pulse wave interval data that have correctly been detected, it is possible to perform various types of biological analyses with a high level of precision. In addition, because the judging process to judge whether the pulse wave signal is influenced by body movements is performed for each pulse beat, the embodiment is suitable for the use in biological analyses that are performed based on every pulse wave interval.

In the exemplary embodiment described above, in the case where a three-axis acceleration sensor is used as the body movement measuring unit 102, the correlation coefficient calculating unit 106 determines, for the mutually different axial directions of the accelerations, the order of priority to be used for calculating the correlation coefficients, at step S17 shown in FIG. 8. Unless the result of the judging process at step S19 is in the affirmative, the correlation coefficient calculating unit 106 then calculates the correlation coefficients by using the accelerations in the axial directions of which the priority level is in third place or higher. However, another arrangement is acceptable in which the correlation coefficient calculating unit 106 calculates the correlation coefficient for the acceleration in the axial direction of which the priority level is in first place, without performing the processes at steps S20 and S21. Also, yet another arrangement is acceptable in which the correlation coefficient calculating unit 106 calculates the correlation coefficients by using the accelerations in the axial directions of which the priority level is in first and second places.

Further, it is acceptable to configure the body movement measuring unit 102 with a device other than the three-axis acceleration sensor. For example, body movements can be measured by using any method with which it is possible to grasp movements of the body. As one example, it is acceptable to detect, in a plurality of contact points, movements of metal ball-like objects that are caused by the body movements. As another example, body movements can be measured by attaching a strain gauge in a joint of the subject, or the like. Further, another arrangement is acceptable in which the body movement measuring unit 102 is configured with a plurality of various types of sensors. In any of these modification examples, an arrangement is acceptable in which the correlation coefficient calculating unit 106 determines an order of priority for a plurality of types of data that have been detected by the single sensor or for a plurality of pieces of data that have been detected by the plurality of sensors so that the data can be used for calculating the correlation coefficients in descending order of the priority levels.

Figure 15:
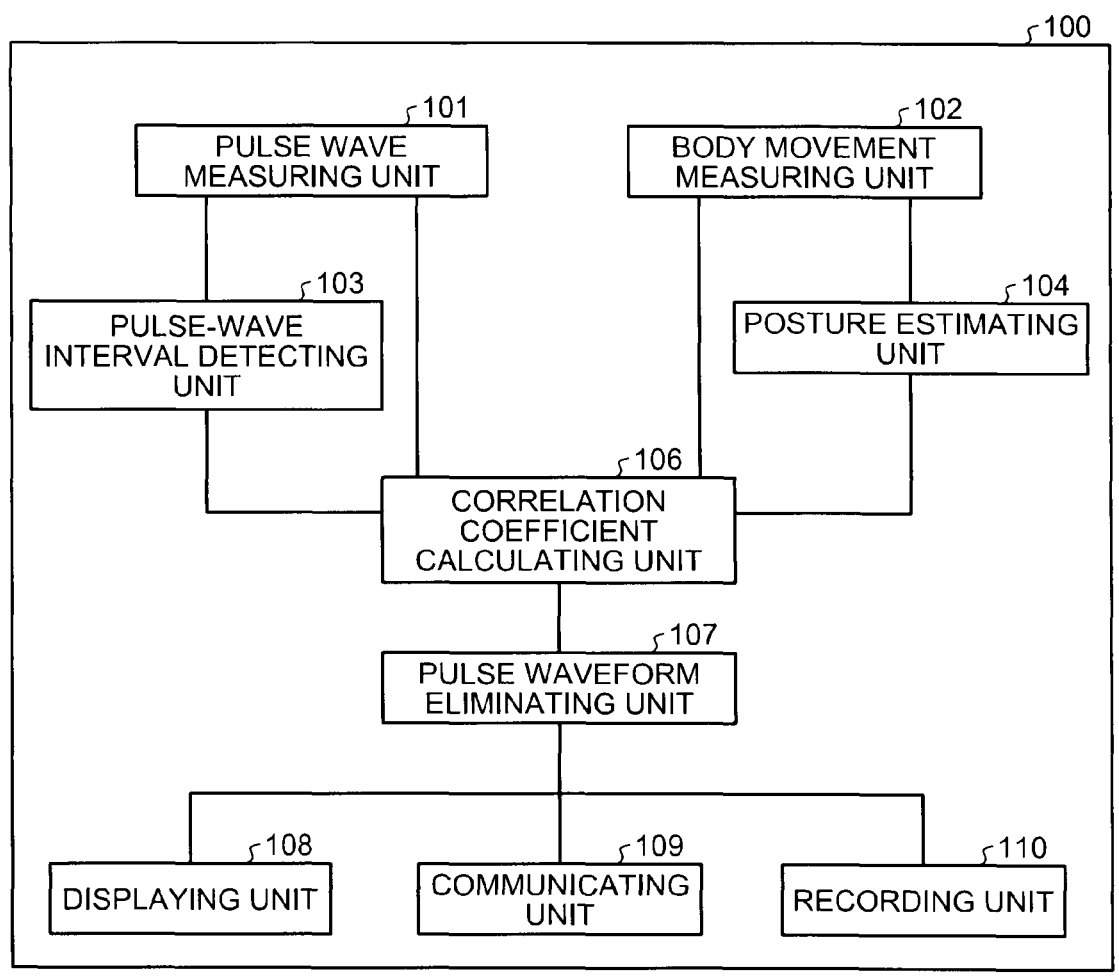
FIG. 15 is a block diagram of the pulse wave processing apparatus according to a modification example.

In the exemplary embodiment described above, it is acceptable to configure the pulse wave processing apparatus 100 so as to include a posture estimating unit. FIG. 15 is a block diagram of the pulse wave processing apparatus 100 according to this modification example. A posture estimating unit 104 shown in FIG. 15 receives, via an input port (not shown), an input of a body movement signal that has been output from the body movement measuring unit 102 and estimates the posture of the subject based on the body movement signal. More specifically, for example, having obtained an acceleration waveform as the body movement signal that has been output from the body movement measuring unit 102, the posture estimating unit 104 estimates the posture of the subject, based on the direct current component obtained through a low-pass filter. Examples of the estimated posture include a supine position, a standing position, and a seated position. An order of priority for the axial directions of the accelerations that are to be used for calculating the correlation coefficients with respect to the pulse wave interval data is determined in advance, in correspondence with the postures of the subject. The order of priority is then stored, in advance, into the recording unit 110 or a memory (not shown).

Figure 16:
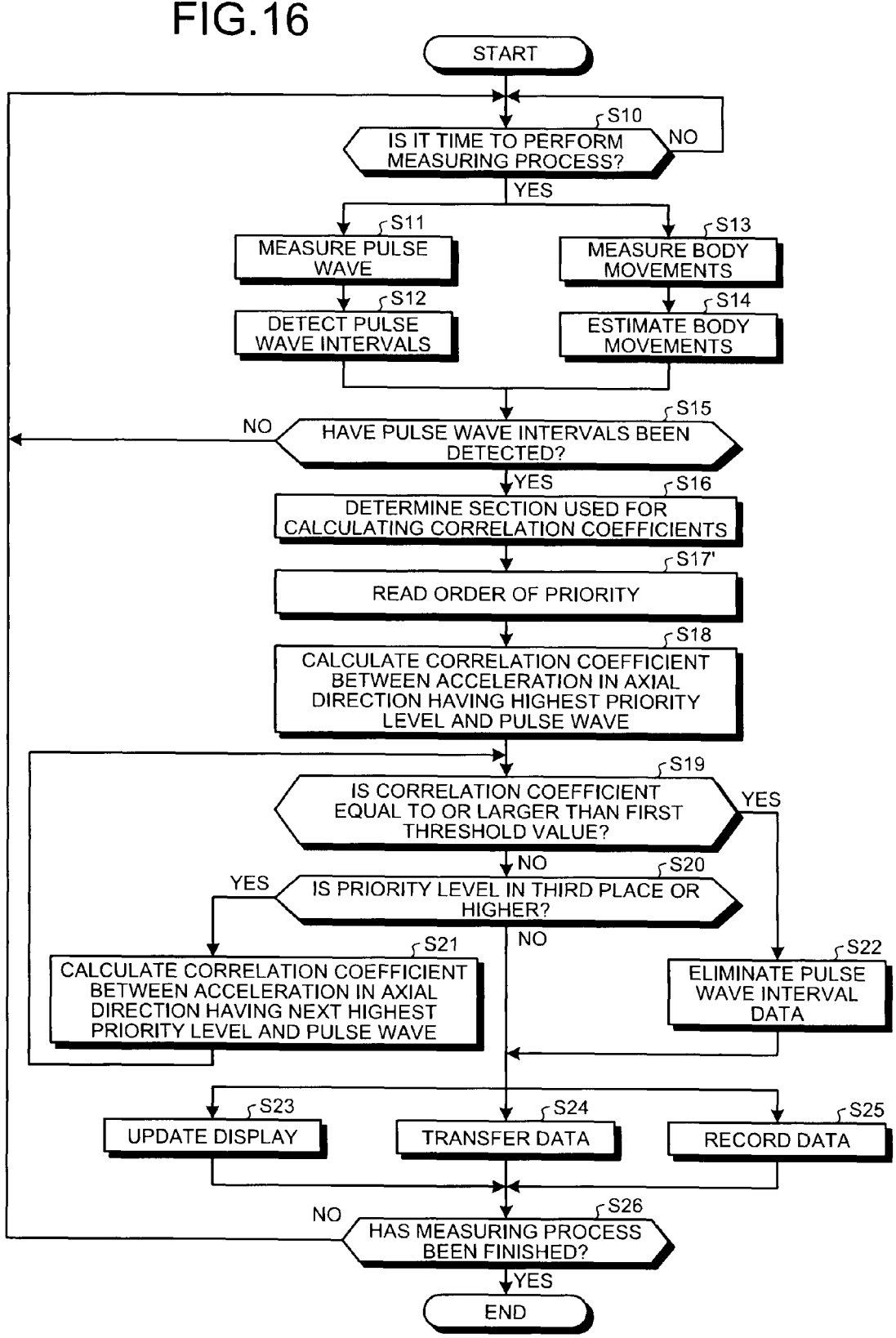
FIG. 16 is a drawing illustrating a procedure in another pulse wave measuring process.

FIG. 16 is a drawing illustrating a procedure in a pulse wave measuring process according to the present modification example. In the present modification example, after the process at step S13 is performed as explained above in the description of the exemplary embodiment, the posture estimating unit 104 estimates the posture of the subject at step S14. After that, at step S17', the correlation coefficient calculating unit 106 calculates a correlation coefficient by using the part of the pulse wave signal within the applicable range that has been determined at step S16 and the part of the acceleration data that corresponds to one of the axial directions having the highest priority level stored in the memory in correspondence with the posture of the subject that has been estimated by the posture estimating unit 104, the part of the acceleration data being selected out of the acceleration data that has been measured by the body movement measuring unit 102 substantially in the same period of time as the part of the pulse wave within the applicable range was measured.

With this arrangement, it is possible to eliminate one or more parts of the pulse wave interval data more appropriately, according to the posture of the subject that greatly influences the pulse waveform.

Also, another arrangement is acceptable in which posture data that expresses the posture estimated by the posture estimating unit 104 is displayed by the displaying unit 108, transmitted to an external information terminal by the communicating unit 109, or stored into the recording unit 110.

According to the present modification example, the posture estimating unit 104 and the correlation coefficient calculating unit 106 are configured as two separate elements. However, another arrangement is acceptable in which the posture estimating unit 104 is included in the correlation coefficient calculating unit 106.

Figure 17:
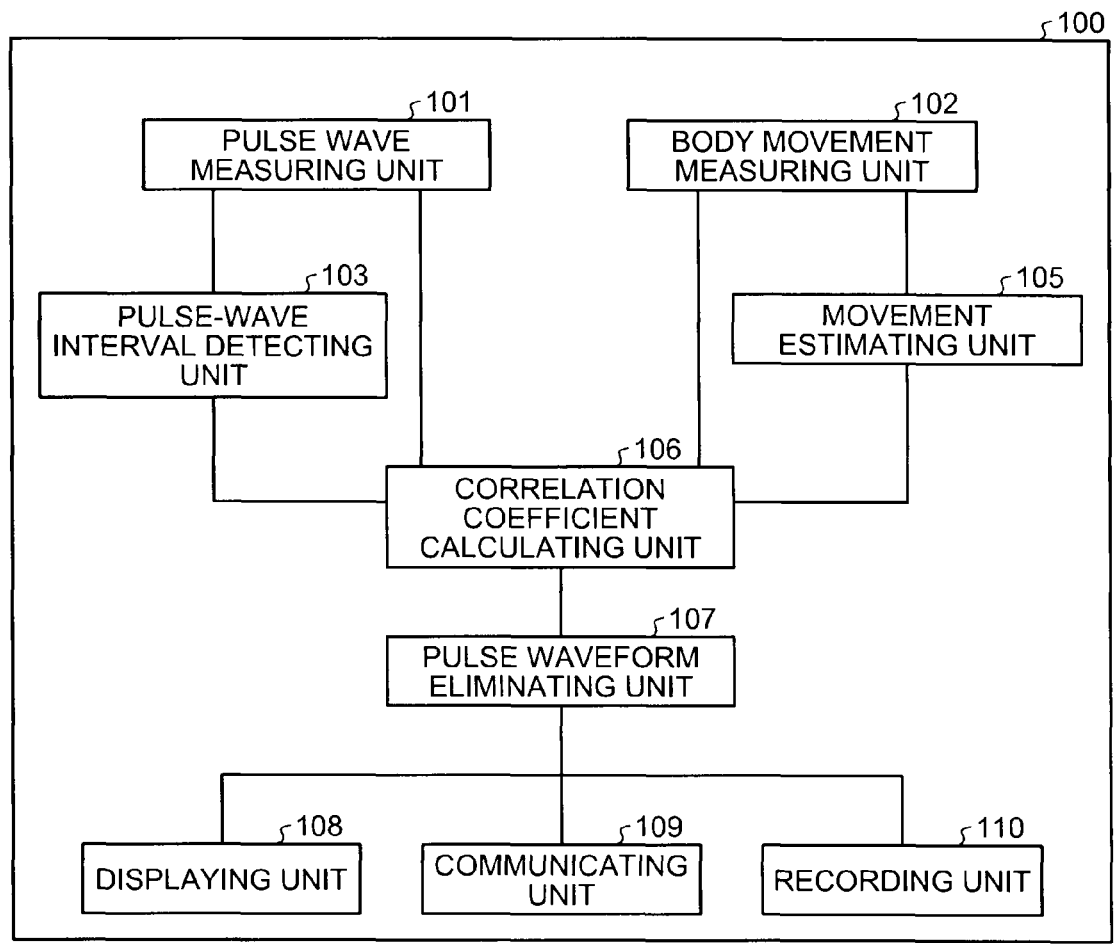
FIG. 17 is a block diagram of the pulse wave processing apparatus according to another modification example.

In the exemplary embodiment described above, it is acceptable to configure the pulse wave processing apparatus 100 so as to include a movement estimating unit. FIG. 17 is a block diagram of the pulse wave processing apparatus 100 according to this modification example. A movement estimating unit 105 shown in FIG. 17 estimates movements of the subject, based on a movement signal that has been output from the body movement measuring unit 102. More specifically, for example, having obtained an acceleration waveform as the body movement signal that has been output from the body movement measuring unit 102, the movement estimating unit 105 estimates the movements of the subject based on the frequency component of the alternating current component obtained through a low-pass filter and the fluctuation pattern. Examples of the estimated movements include walking (walking normally or walking while carrying an object in the arms), walking up or down steps, running, riding a bicycle, riding in an automobile, and riding in a train. An order of priority for the axial directions of the accelerations that are to be used for calculating the correlation coefficients with respect to the pulse wave signal is determined in advance, in correspondence with the movements of the subject. The order of priority is then stored, in advance, into the recording unit 110 or a memory (not shown).

An example of the configuration of the movement estimating unit 105 is disclosed in JP-A 2001-344352 (KOKAI). Further, in the case where the body movement measuring unit 102 is worn around a wrist of the subject, it is a good idea to configure the movement estimating unit 105 by using, in particular, the technique disclosed in the document listed below:

Makoto SATO, Chie MORITA, and Miwako DOI: "Seitai DATA to Kasokudo DATA o mochiita koudou ninshiki" (Behavior Recognition using Biological Data and Acceleration Data), Proceedings of the 65th National convention of Information Processing Society of Japan, 3T5B-2, pp. 239-242 (March 2003).

The procedure in the pulse wave measuring process according to the present modification example is substantially similar to the one shown in FIG. 16. More specifically, in the present modification example, after the process at step S13 is performed as explained above in the description of the exemplary embodiment, the movement estimating unit 105 estimates the movements of the subject at step S14. After that, at step S17', the correlation coefficient calculating unit 106 calculates a correlation coefficient by using the part of the pulse wave signal within the applicable range that has been determined at step S16 and the part of the acceleration data that corresponds to one of the axial directions having the highest priority level stored in the memory in correspondence with the movements of the subject that have been estimated by the movement estimating unit 105, the part of the acceleration data being selected out of the acceleration data that has been measured by the body movement measuring unit 102 substantially in the same period of time as the part of the pulse wave within the applicable range was measured.

With this arrangement, it is possible to eliminate one or more parts of the pulse wave interval data more appropriately, according to the movements of the subject that greatly influence the pulse waveform.

Also, another arrangement is acceptable in which movement data that expresses the movements estimated by the movement estimating unit 105 is displayed by the displaying unit 108, transmitted to an external information terminal by the communicating unit 109, or stored into the recording unit 110.

According to the present modification example, the movement estimating unit 105 and the correlation coefficient calculating unit 106 are configured as two separate elements. However, another arrangement is acceptable in which the movement estimating unit 105 is included in the correlation coefficient calculating unit 106.

In the exemplary embodiment described above, the pulse wave processing apparatus 100 includes the pulse-wave interval detecting unit 103 so that the pulse waveform eliminating unit 107 eliminates, as necessary, one or more parts of the pulse wave interval data, based on the correlation coefficients.

However, another arrangement is acceptable in which the pulse wave processing apparatus 100 does not include the pulse-wave interval detecting unit 103, but the pulse waveform eliminating unit 107 eliminates, as necessary, one or more parts of the pulse wave signal itself that has been output from the pulse wave measuring unit 101, based on the correlation coefficients.

In the exemplary embodiment described above, the pulse wave processing apparatus 100 is configured so as to include the displaying unit 108, the communicating unit 109, and the recording unit 110 as output units. However, another arrangement is acceptable in which the pulse wave processing apparatus 100 includes none or only one or two of these output units. Further, in the case where the pulse wave processing apparatus 100 includes the displaying unit 108 and the communicating unit 109, an arrangement is acceptable in which the communicating unit 109 does not necessarily transfer the pulse wave interval data to an external information terminal immediately.

Furthermore, in the exemplary embodiment described above, another arrangement is acceptable in which the pulse wave processing apparatus 100 is configured so as to include a converting unit that converts the pulse wave interval data into a pulse rate, so that the pulse rate that is converted by the converting unit from the one or more parts of the pulse wave interval data that have been adopted by the pulse waveform eliminating unit 107 out of the pulse wave interval data detected by the pulse-wave interval detecting unit 103 is output to at least one of the displaying unit 108, the communicating unit 109, and the recording unit 110.

Figure 18:
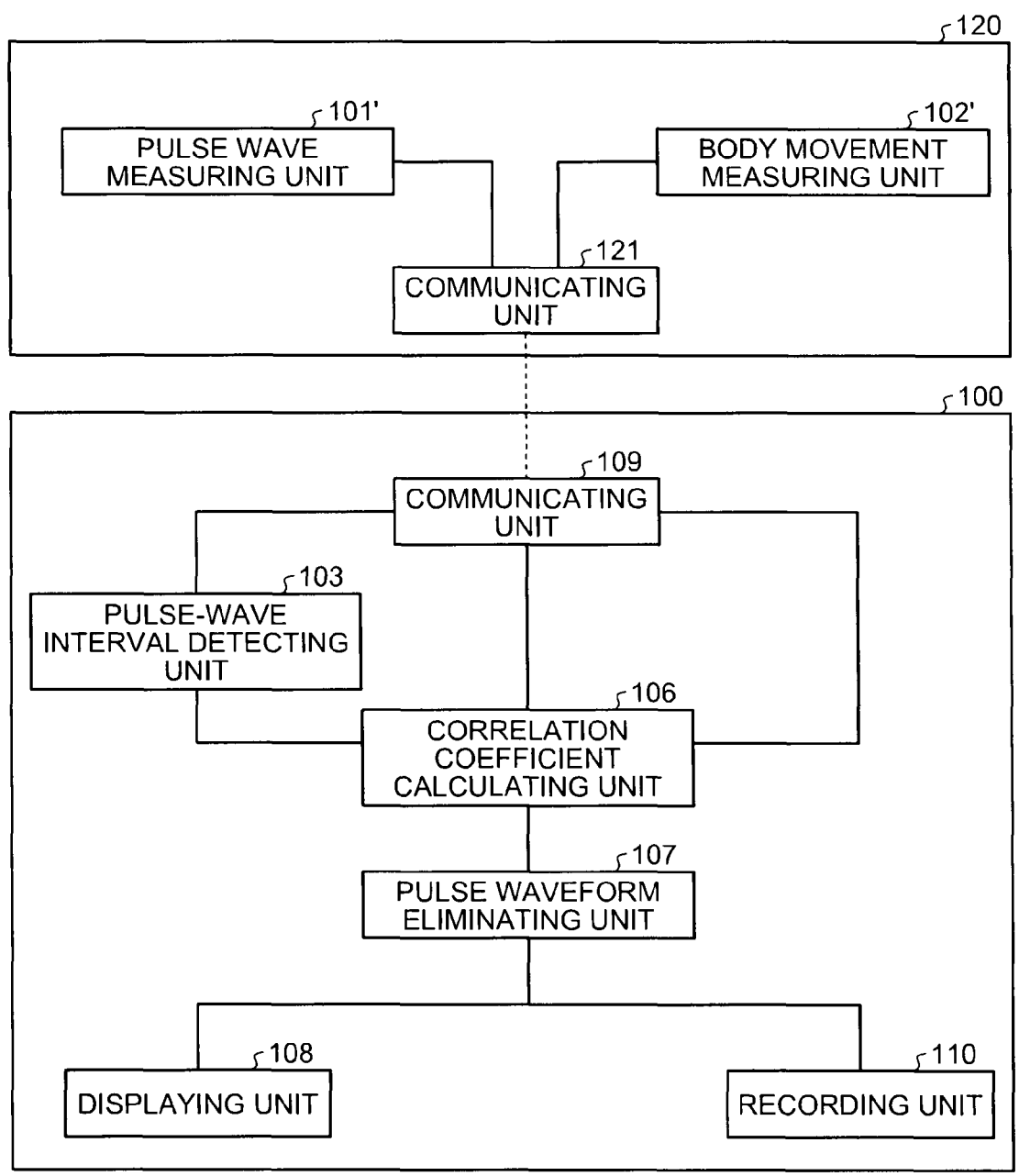
FIG. 18 is a block diagram of the pulse wave processing apparatus according to yet another modification example and a pulse wave measuring apparatus that is an external apparatus.

In addition, in the exemplary embodiment described above, the pulse wave processing apparatus 100 is configured so as to include the pulse wave measuring unit 101 and the body movement measuring unit 102 so that the pulse wave processing apparatus 100 also functions as a pulse wave measuring apparatus. However, another arrangement is acceptable in which the pulse wave processing apparatus 100 does not include these units and obtains the pulse wave signal and the body movement signal by employing an external apparatus. FIG. 18 is a block diagram of the pulse wave processing apparatus 100 according to the present modification example and a pulse wave measuring apparatus 120 that is the external apparatus. The pulse wave measuring apparatus 120 includes a pulse wave measuring unit 101', a body movement measuring unit 102', and a communicating unit 121 that is configured with, for example, a network interface. The configurations of the pulse wave measuring unit 101' and the body movement measuring unit 102' are substantially the same as the configurations of the pulse wave measuring unit 101 and the body movement measuring unit 102, respectively, that are described above. The pulse wave measuring apparatus 120 transmits the pulse wave signal that has been output from the pulse wave measuring unit 101' and the body movement signal that has been output from the body movement measuring unit 102' to the pulse wave processing apparatus 100 via the communicating unit 121. The pulse wave processing apparatus 100 receives the pulse wave signal and the body movement signal from the pulse wave measuring apparatus 120 via the communicating unit 109. The pulse wave processing unit 100 detects pulse wave intervals by using the received pulse wave signal and calculates correlation coefficients by using the pulse wave signal and the body movement signal that have been received, in the same manner as described in the exemplary embodiment. Further, based on the calculated correlation coefficients, the pulse wave processing unit 100 eliminates one or more parts of the pulse wave interval data corresponding to one or more parts of the pulse wave signal that are greatly influenced by the body movements.

In the present modification example, another arrangement is acceptable in which the pulse wave processing apparatus 100 further includes one or both of the posture estimating unit 104 and the movement estimating unit 105 that are explained in the second and the third modification examples described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pulse wave processing apparatus comprising:
   an obtaining unit that obtains pulse wave signal data expressing a pulse wave of a subject and body movement signal data expressing body movements of the subject;
   a correlation coefficient calculating unit that calculates a correlation coefficient expressing a degree of correlation between the pulse wave signal data and the body movement signal data; and
   a pulse wave eliminating unit that eliminates one or more pieces of the pulse wave signal data in which the correlation coefficient is equal to or larger than a predetermined threshold value.

2. The apparatus according to claim 1, further comprising a pulse-wave interval detecting unit that detects first pulse wave interval data for each pulse beat by using a waveform of the pulse wave expressed by the pulse wave signal data, wherein
   the pulse wave eliminating unit calculates third pulse wave interval data that is obtained by eliminating second pulse wave interval data from the first pulse wave interval data, the second pulse wave interval data expressing a pulse wave interval in which the correlation coefficient is equal to or larger than a predetermined threshold value.

3. The apparatus according to claim 2, wherein the correlation coefficient calculating unit calculates the correlation coefficient at a time when a pulse wave interval for the each pulse beat is detected.

4. The apparatus according to claim 2, wherein
   the correlation coefficient calculating unit determines an applicable range of the pulse wave signal data that is to be used for calculating the correlation coefficient, based on the first pulse wave interval data, and calculates the correlation coefficient by using a piece of the pulse wave signal data within the determined applicable range.

5. The apparatus according to claim 1, wherein
   the body movement signal data includes a plurality of pieces of signal data, and
   the correlation coefficient calculating unit determines a priority level of at least one of the pieces of signal data, and calculates the correlation coefficient expressing the degree of correlation between at least one of the pieces of signal data having a highest priority level and the pulse wave signal data.

6. The apparatus according to claim 5, wherein
   the pulse wave processing apparatus further comprises a posture estimating unit that estimates a posture of the subject based on the body movement signal,
   the correlation coefficient calculating unit determines the priority levels of the pieces of signal data according to a descending order of a degree of correlation between each of the pieces of signal data and the estimated posture of the subject, and calculates the correlation coefficient expressing the degree of correlation between at least one of the pieces of signal data having a highest priority level and the pulse wave signal data.

7. The apparatus according to claim 5, wherein
   the pulse wave processing apparatus further comprises a movement estimating unit that estimates a movement of the subject based on the body movement signal,
   the correlation coefficient calculating unit determines the priority levels of the pieces of signal data according to a descending order of a degree of correlation between each of the pieces of signal data and the estimated movement of the subject, and calculates the correlation coefficient expressing the degree of correlation between at least one of the pieces of signal data having a highest priority level and the pulse wave signal data.

8. The apparatus according to claim 2, further comprising an output unit that outputs at least one of the pulse wave signal data, the body movement signal data, and the third pulse wave interval data.

9. The apparatus according to claim 8, further comprising an output unit that outputs posture data expressing an estimated posture of the subject.

10. The apparatus according to claim 8, further comprising an output unit that outputs movement data expressing an estimated movement of the subject.

11. The apparatus according to claim 1, further comprising a pulse wave measuring unit that measures a pulse wave of the subject and outputs the pulse wave signal data expressing the pulse wave, wherein
    the obtaining unit obtains the pulse wave signal data output from the pulse wave measuring unit.

12. The apparatus according to claim 1, further comprising a movement measuring unit that measures a movement of the subject and outputs the movement signal data expressing the movement, wherein
    the obtaining unit obtains the movement signal data output from the movement measuring unit.

13. The apparatus according to claim 12, wherein
    the body movement measuring unit includes a three-axis acceleration sensor and measures accelerations in three axial directions that are orthogonal to one another, and outputs, as the body movement signal data, a signal that contains data of the accelerations in the three axial directions as signal data.

14. A pulse wave processing method executed by a pulse wave processing apparatus that includes an obtaining unit, a correlation coefficient calculating unit, and a pulse wave eliminating unit, the method comprising:
    obtaining pulse wave signal data expressing a pulse wave of a subject and body movement signal data expressing body movement of the subject by employing the obtaining unit;
    calculating a correlation coefficient expressing a degree of correlation between the pulse wave signal data and the body movement signal data by employing the correlation coefficient calculating unit; and
    eliminating one or more pieces of the pulse wave signal data in which the correlation coefficient is equal to or larger than a predetermined threshold value by employing the pulse wave eliminating unit.

* * * * *